(12) United States Patent
Moffat et al.

(10) Patent No.: US 10,758,536 B2
(45) Date of Patent: Sep. 1, 2020

(54) METHOD FOR TREATING SHINGLES WITH N-METHANOCARBATHYMIDINE (N-MCT)

(71) Applicant: N&N PHARMACEUTICALS INC., Rockville, MD (US)

(72) Inventors: Jennifer Moffat, Syracuse, NY (US); Dongmei Liu, Syracuse, NY (US); Wanda Coombs, Syracuse, NY (US); Michael Appel, Syracuse, NY (US); Aquilur Rahman, Rockville, MD (US)

(73) Assignee: L & J Bio Inc, Seoul (KR)

( * ) Notice: Subject to any disclaimer, the term of this patent is extended or adjusted under 35 U.S.C. 154(b) by 0 days.

(21) Appl. No.: 15/145,426

(22) Filed: May 3, 2016

(65) Prior Publication Data
US 2016/0324857 A1 Nov. 10, 2016

Related U.S. Application Data

(60) Provisional application No. 62/156,773, filed on May 4, 2015.

(51) Int. Cl.
*A61K 31/513* (2006.01)
*A61K 9/00* (2006.01)
*A61K 9/06* (2006.01)

(52) U.S. Cl.
CPC .......... *A61K 31/513* (2013.01); *A61K 9/0014* (2013.01); *A61K 9/0019* (2013.01); *A61K 9/06* (2013.01)

(58) Field of Classification Search
CPC .. A61K 31/513; A61K 9/0053; A61K 9/0014; A61K 9/06; A61K 9/0019
See application file for complete search history.

(56) References Cited

U.S. PATENT DOCUMENTS 5,629,454 A 5/1997 Marquez et al.
5,840,728 A * 11/1998 Marquez ................ A61K 31/44
                                              514/263.37

FOREIGN PATENT DOCUMENTS

WO 1995/08541 A1 3/1995

OTHER PUBLICATIONS

Andrei, G., Sienaert, R., McGuigan, C., De Clercq, E., Balzarini, J., Snoeck, R., 2005. Susceptibilities of several clinical varicella-zoster virus (VZV) isolates and drug-resistant VZV strains to bicyclic furano pyrimidine nucleosides. Antimicrobial agents and chemotherapy 49, 1081-1086.
Bernstein, D.I., Bravo, F.J., Clark, J.R., Earwood, J.D., Rahman, A., Glazer, R., Cardin, R.D., 2011. N-Methanocarbathymidine is more effective than acyclovir for treating neonatal herpes simplex virus infection in guinea pigs. Antiviral Research 92, 386-388.
Hambleton, S., Steinberg, S.P., Gershon, M.D., Gershon, A.A., 2007. Cholesterol dependence of varicella-zoster virion entry into target cells. Journal of virology 81, 7548-7558.
Johnson, B.H., Palmer, L., Gatwood, J., Lenhart, G., Kawai, K., Acosta, C.J. 2015. Annual incidence rates of herpes zoster among an immunocompetent population in the United States. BMC Infect Dis 15: 502.
Kim, S.R., Khan, F., Tyring, S.K. 2014. Varicella zoster: an update on current treatment options and future perspectives, Expert Opin on Pharmacother, 15:1, 61-71.
Marquez, V.E., Hughes, S.H., Sei, S., Agbaria, R., 2006. The history of N-methanocarbathymidine: the investigation of a conformational concept leads to the discovery of a potent and selective nucleoside antiviral agent. Antiviral research 71, 268-275.
Prichard, M. N., K. A. Keith, D. C. Quenelle and E. R. Kern (2006). "Activity and mechanism of action of N-methanocarbathymidine against herpesvirus and orthopoxvirus infections." Antimicrob Agents Chemother 50(4): 1336-1341.
Quenelle, D.C., Collins, D.J., Rice, T.L., Rahman, A., Glazer, R., 2011. Efficacy of orally administered low dose N-methanocarbathymidine against lethal herpes simplex virus type-2 infections of mice. Antiviral chemistry & chemotherapy 22, 131-137.
Rowe J, Greenblatt RJ, Liu D, Moffat JF. Compounds that target host cell proteins prevent varicella-zoster virus replication in culture, ex vivo, and in SCID-Hu mice. Antiviral Res. Jun. 2010;86(3):276-85.
Schmader, K., and Dworkin, R. 2008. Natural history and treatment of herpes zoster. J. Pain Supp. 1: S3-S9.
Taylor, S. L. and J. F. Moffat (2005). "Replication of varicella-zoster virus in human skin organ culture." J Virol 79(17): 11501-11506.
Wang, W., S. L. Taylor, S. A. Leisenfelder, R. Morton, J. F. Moffat, S. Smirnov and H. Zhu (2005). "Human cytomegalovirus genes in the 15-kilobase region are required for viral replication in implanted human tissues in SCID mice." J Virol 79(4): 2115-2123.
Zhang, Z., Rowe, J., Wang, W., Sommer, M., Arvin, A., Moffat, J., Zhu, H., 2007. Genetic analysis of varicella-zoster virus ORF0 to ORF4 by use of a novel luciferase bacterial artificial chromosome system. J. Virol. 81, 9024-9033.

* cited by examiner

Primary Examiner — Sudhakar Katakam
(74) Attorney, Agent, or Firm — Nixon & Vanderhye, P.C.

(57) ABSTRACT

The present application discloses a method of treating a Varicella-Zoster Virus (VZV) infection in an individual in need thereof, including the step of administering to said individual an effective Varicella-Zoster Virus antiviral amount of a compound called N-methanocarbathymidine (N-MCT), which has a northern configuration with the structure as follows

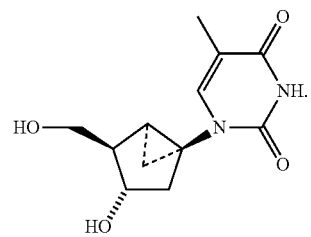

21 Claims, 12 Drawing Sheets

N-MCT prevents VZV growth in skin organ culture

FIG. 2

Assays 4 and 5
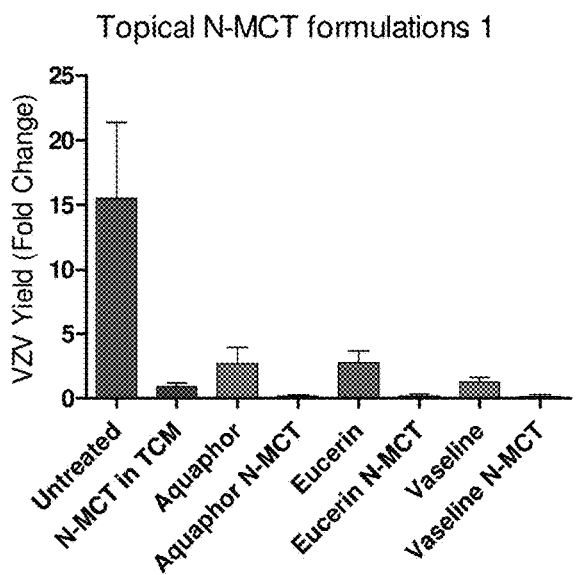
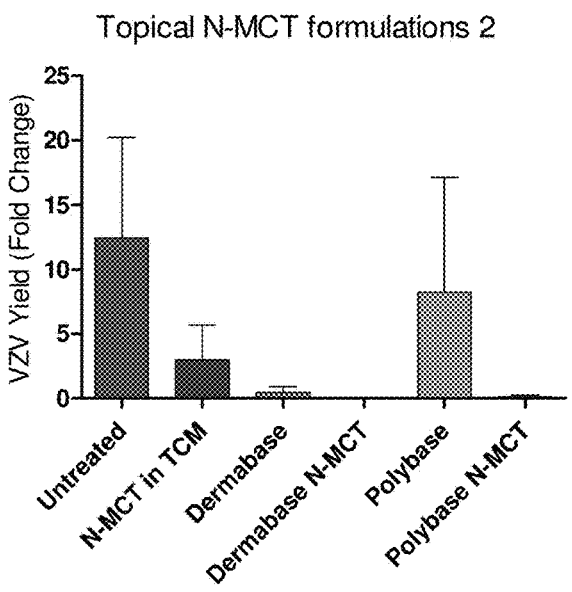
FIG. 6A
FIG. 6B

FIG. 7A N-MCT is effective an effective topical treatment for VZV in skin

FIG. 7B Repeat Assay: 5 Days Topical N-MCT is Effective

FIG. 7C VZV Rebound after Topical N-MCT Treatment

METHOD FOR TREATING SHINGLES WITH N-METHANOCARBATHYMIDINE (N-MCT)

CROSS REFERENCE TO RELATED APPLICATIONS

The present application is a non-provisional of U.S. Provisional Application Ser. No. 62/156,773 filed May 4, 2015, the contents of which are incorporated by reference herein in their entirety.

BACKGROUND OF THE INVENTION

1. Field of the Invention

The present invention relates to the use of conformationally locked nucleoside analog, in particular, N-MCT, as antiviral agent for the treatment of shingles. More specifically, the invention relates to the use of 2'-deoxynucleoside analogs in particular, N-MCT, locked in the Northern conformation as anti-varicella-zoster virus (VZV) agents.

2. General Background and State of the Art

Nucleoside analogs lacking 2'- and 3'-hydroxyl groups (dideoxynucleosides), as well as those 2'-deoxynucleosides where the 3'-hydroxyl function has been chemically modified or changed, can function as chain terminators of DNA synthesis after their incorporation into DNA. This is the basis of the Sanger dideoxynucleotide method for DNA sequencing (Sanger et al., Proc. Natl. Acad. Sci. USA, 1977).

Altmann et al. (Tetrahedron Lett., 35:2331-2334, 1994) demonstrated that substitution of N-methanocarba-thymidine (N-methanocarba-T) for thymidine in DNA/RNA heteroduplexes increased the thermodynamic stability of the double helix, as indicated by a positive increase in the $T_m$, whereas the Southern conformer induced a small destabilizing effect (Altmann et al., Tetrahedron Lett., 35:7625-7628, 1994).

The conformationally (Northern) locked nucleoside analogs for use in the present invention are described in U.S. Pat. Nos. 5,629,454, and 5,840,728, and Published International Application No. PCT WO95/08541.

The lifetime risk of shingles for an immunocompetent person living in the U.S. is approximately 30%, and a million cases of shingles are diagnosed each year (Johnson, et al., BMC Infect Dis, 15:502-507, 2015, PMCID: PMC4636742). Antiviral therapy for acute shingles should be started as soon as possible after diagnosis to reduce major complications such as postherpetic neuralgia (PHN). Although existing antivirals lessen the severity of PHN when therapy begins early, more effective antiviral drugs are needed to prevent the worst sequelae of shingles (Kim, et al, Expert Opin. Pharmacother., 15:61-71, 2014, PMID: 24289750).

Studies of pain severity have shown that PHN exceeds childbirth, musculoskeletal pain, osteoarthritis and chronic cancer pain. In one study, 42% of patients referred to their worst shingles pain as "horrible" or "excruciating". As pain levels increase, the person is more likely to have a decline in physical and social functioning and an increase in emotional distress. Patients with more severe pain during the initial stage of shingles may be at higher risk for developing PHN.

Research puts shingles and postherpetic neuralgia on a par with congestive heart failure, diabetes and depression for disrupting a person's quality of life. Thus, shingles can have a major impact on morbidity, lost work productivity and quality of life in older adults. Active people may end up in a nursing home due to PHN.

In addition to the excruciating pain of PHN, other complications of shingles may include scarring, secondary bacterial infections, pneumonia, visual and hearing impairments and, rarely, death. If left untreated, 10% of patients whose shingles affects an eye will experience severe visual loss, eyelid scarring or chronic in-turning of the eyelashes. Although shingles is not highly communicable, it is a public health concern because of the serious complications, the detrimental impact on quality of life, and the cost of care. The Agency for Healthcare Research and Quality recently estimated that an average of $566 million per year is spent on health care for shingles and its complications. Another study estimated that the overall costs of shingles and PHN may be as high as $1.7 billion a year, including health care costs and productivity losses.

There is a constant need for new and effective antiviral agents to treat shingles by preventing replication of varicella-zoster virus. The present invention provides such agent.

SUMMARY OF THE INVENTION

One embodiment of the present invention is a method of treating a VZV infection in an individual in need thereof, comprising the step of administering to said individual an effective VZV antiviral amount of a compound having the formula

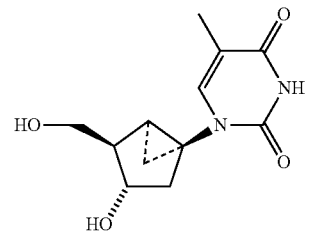

or a substituted derivative thereof in a pharmaceutically acceptable carrier, said compound locked in the Northern conformation. Preferably, the effective amount is between about 600 mg and about 15,000 mg per day orally. Advantageously, the administering step is, oral, intravenous, topical, intramuscular or subcutaneous.

In one aspect, the invention is directed to a method of treating shingles in an individual in need thereof, comprising the step of administering to said individual an effective antiviral compound called N-methanocarbathymidine (N-MCT), which has a northern configuration with the structure as follows in a therapeutically effective dose.

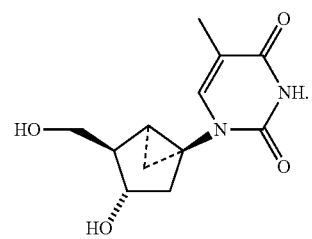

Shingles may be treated with optimal dose of N-MCT to lessen the severity of or to prevent postherpetic neuralgia (PHN) and debilitating pain. The administering step may be oral, intravenous, topical, intramuscular or subcutaneous. The effective oral amount for a human suffering from symptoms of shingles may be between about 600 mg and about 2,000 mg per day, or between about 600 mg and about 1,500 mg per day.

Another embodiment of the invention is a pharmaceutical composition comprising the compound shown above in a pharmaceutically acceptable carrier. Preferably, the carrier is suitable for oral administration, additionally the carrier is also a sterile carrier suitable for parenteral administration. Alternatively, the carrier is suitable for topical administration.

The present application also includes a method of simultaneously treating the shingles with any of the administrative methods above.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 2 shows that N-MCT prevents VZV growth in skin organ culture.

FIG. 3A shows the in vivo VZV growth preventative effects of N-MCT at concentrations of 5, 10, 20, 25, 50 and 100 mg/kg. FIG. 3B shows the in vivo VZV yield reductive effects of N-MCT at day 6 post infection, at concentrations of 5, 10, 20, 25, 50 and 100 mg/kg.

FIG. 4A shows the in vivo VZV growth preventative effects of N-MCT at concentrations of 25 mg/kg, 50 mg/kg, and 100 mg/kg. FIG. 4B shows the in vivo VZV growth preventative effects of N-MCT at concentrations of 5 mg/kg, 10 mg/kg, and 20 mg/kg.

FIG. 5A shows 0.5% Cidofovir, 0.05% N-MCT, 0.5% N-MCT, and 5% N-MCT were tested. FIG. 5B shows delayed treatment effects of 0.5% N-MCT in carbopol with 10% HPBCD. FIG. 5C shows effects of 1% DMSO and 10% HPBCD in carbopol gel, and 0.5% N-MCT in either vehicle. The positive control Cidofovir is no longer being used to treat Shingles in human beings and has been abandoned by its drug maker due to its high level of toxicity. Each line represents the average Total Flux for the group. The error bars are the standard deviation of the mean. The fold-change was calculated from the average Total Flux value for all samples on Day 1, which is before any treatments were begun. Each value was then divided by this starting value to determine the change in VZV yield.

FIGS. 6A-6B show various formulations for topical treatment of 0.5% N-MCT on skin organ culture. FIG. 6A shows results with 0.5% N-MCT in Aquaphor, Eucerin, and Vaseline. FIG. 6B shows results with 0.5% N-MCT in Dermabase, and Polybase.

FIGS. 7A-7C show effectiveness of topical treatment for VZV in skin organ culture. FIG. 7A shows VZV yield at day 5 after treatment with Aquaphor, Eucerin, and Dermabase. FIG. 7B shows the results of repeat experiment. FIG. 7C shows the VZV rebound activity after topical N-MCT treatment.

FIGS. 8A-8C show that N-MCT is effective in vivo even when treatment with N-MCT is delayed 3 or 7 days after VZV infection.

DETAILED DESCRIPTION OF THE PREFERRED EMBODIMENTS

In the present application, "a" and "an" are used to refer to both single and a plurality of objects.

As used herein, "shingles" caused by varicella-zoster virus (VZV) is an outbreak of rash or blisters on the skin. The first sign of shingles is often burning or tingling pain, or sometimes numbness or itch, in one particular location on only one side of the body. After several days or a week or more, of nerve pain, a rash of fluid-filled blisters, similar to chickenpox, appear in one area on one side of the body. Shingles pain can be mild or intense and may persist with debilitating effect. The most common location for shingles is a band, called a dermatome, spanning one side of the trunk around the waistline. During primary infection with VZV, known as chicken pox, the virus infects the nervous system and establishes lifelong latency. When the virus reactivates, it migrates along the long nerve fibers that extend from the sensory cell bodies to the skin. VZV replication in the skin causes eruption of the tell-tale rash of herpes zoster, and the person now has shingles. The cause of debilitating pain in the nerve is thought to be due to VZV replication in the sensory neurons and in skin cells.

Postherpetic neuralgia (PHN) is a condition of recurring or persistent pain in an area of the body that has undergone an outbreak of herpes zoster (HZ), caused by the varicella zoster virus, commonly termed shingles. It usually begins after shingles lesions (blisters) begin to crust over and heal but may occur in some patients who do not produce lesions. Some investigators suggest the pain has to be present for three months to be termed PHN.

There is a large demand for new antiviral drugs that can limit the spread of VZV in skin, especially since the currently approved drugs do little to halt the replication of this virus. For instance, acyclovir and its derivatives are prescribed for VZV infections, but are only marginally effective. It is commonly known that the $EC_{50}$ for acyclovir is 10-fold higher for VZV than for HSV-1 (Andrei et al., 2005).

The N-Methanocarbathymidine (N-MCT) compound that is used in the practice of the present invention is described in U.S. Pat. Nos. 5,629,454, and 5,840,728, and Published International Application No. PCT WO95/08541, the entire contents of which are hereby incorporated by reference.

The synthesis of the (N)-methanocarba-adenosine, guanine, cytidine, thymidine and uridine analogs are described in Examples 1 to 19 in U.S. Pat. No. 5,840,728 and in Schemes 1-4 shown in columns 7 to 10 in U.S. Pat. No. 5,840,728, which are incorporated by reference herein.

The anti-VZV effect of N-MCT is unique. The compound has profound activity against VZV, which can solve a major public health concern. The N-MCT or derivatives thereof, or pharmaceutically acceptable esters or salts of these compounds, may be incorporated into a pharmaceutically acceptable carrier for administration to an individual having a VZV infection. Contemplated routes of administration include oral, topical, intravenous, intramuscular and subcutaneous. Nonlimiting examples of particularly preferred nucleoside analog compositions for topical administration include creams, lotions, gels, salves, sprays, dispersions, suspensions, pastes and ointments.

Figure 1:
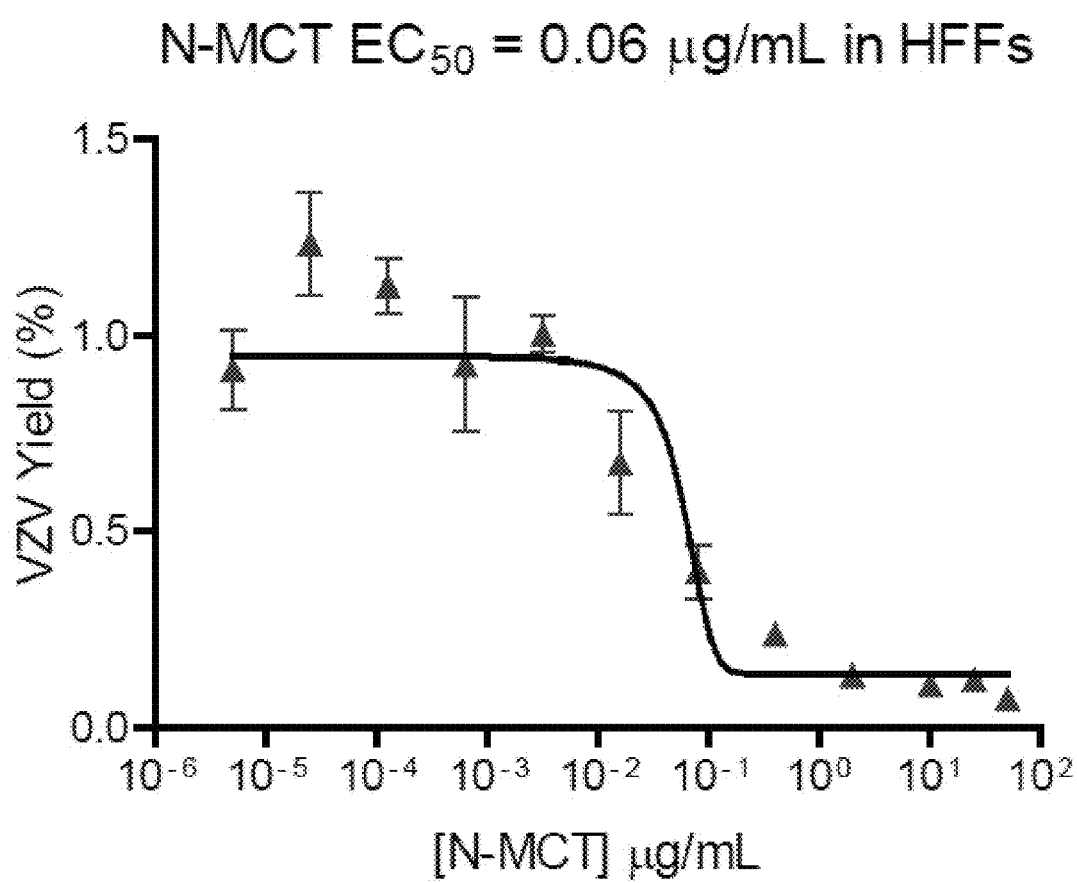
FIG. 1 shows sensitivity of VZV to N-MCT with an $EC_{50}$=0.06 μg/ml in human foreskin fibroblasts.
Figure 3A:
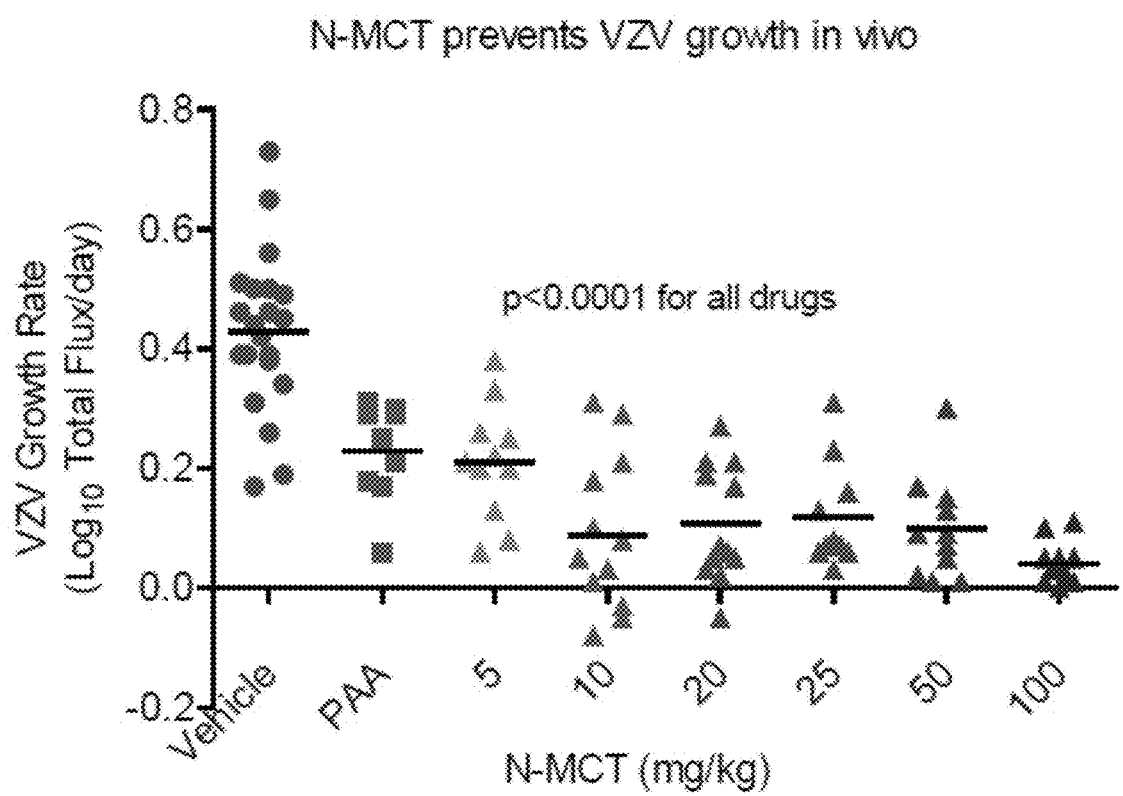
FIGS. 3A-3B show the effectiveness of N-MCT in vivo against VZV in SCID-Hu mice.
Figure 3B:
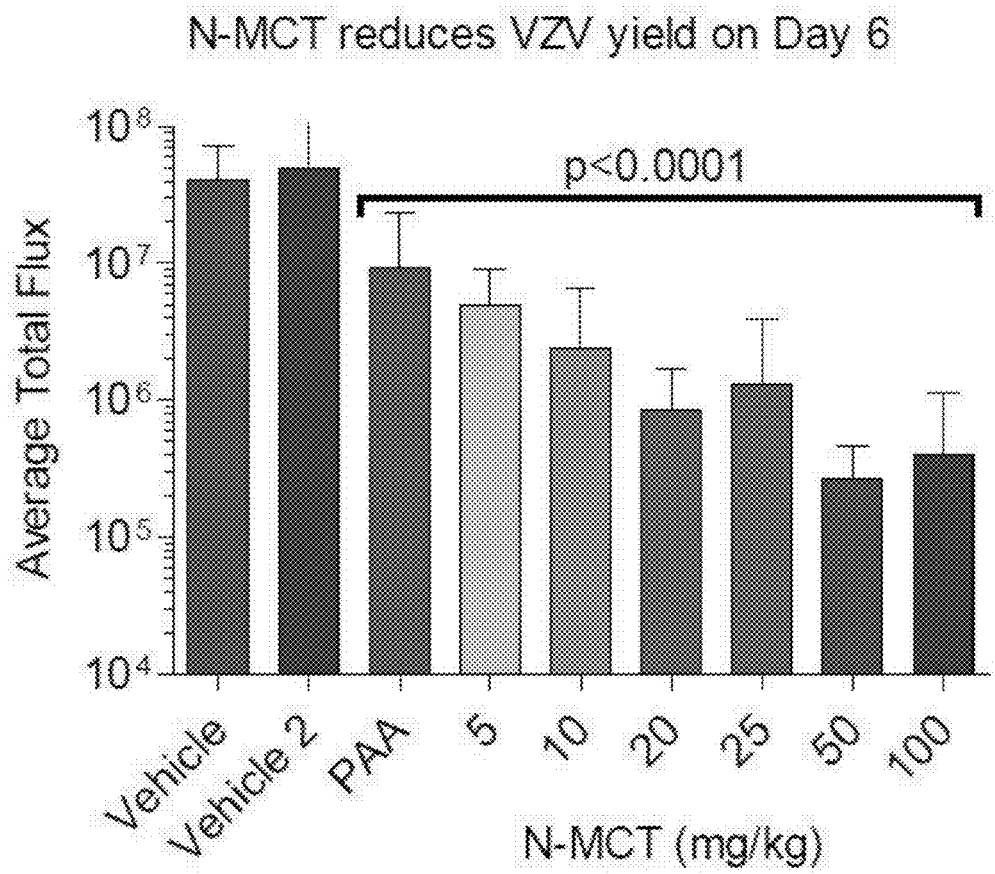
Figure 4A:
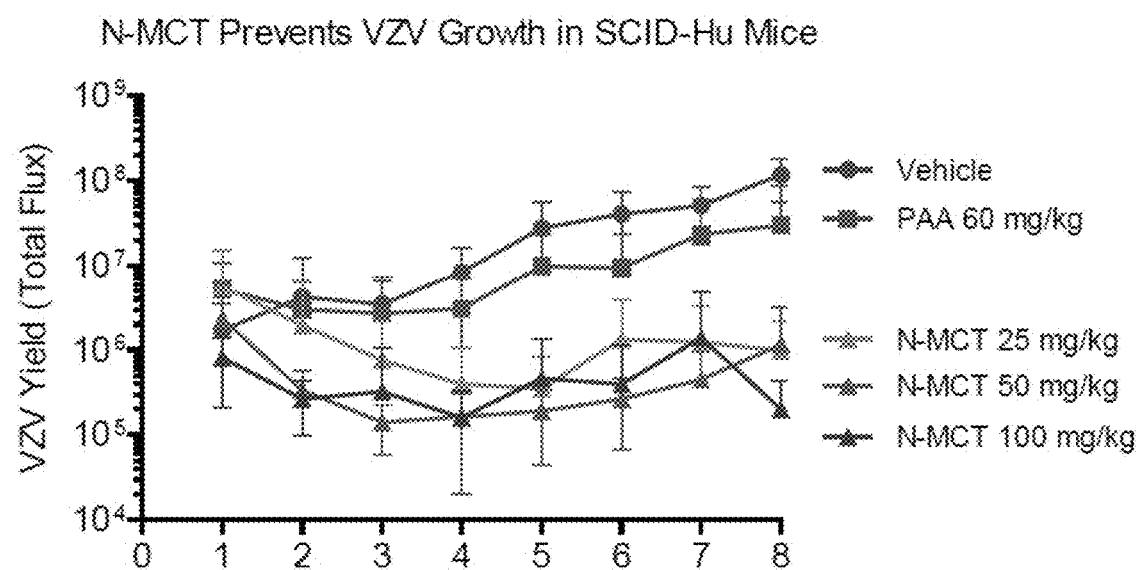
FIGS. 4A-4B show the effectiveness of N-MCT in vivo against VZV in SCID-Hu mice.
Figure 4B:
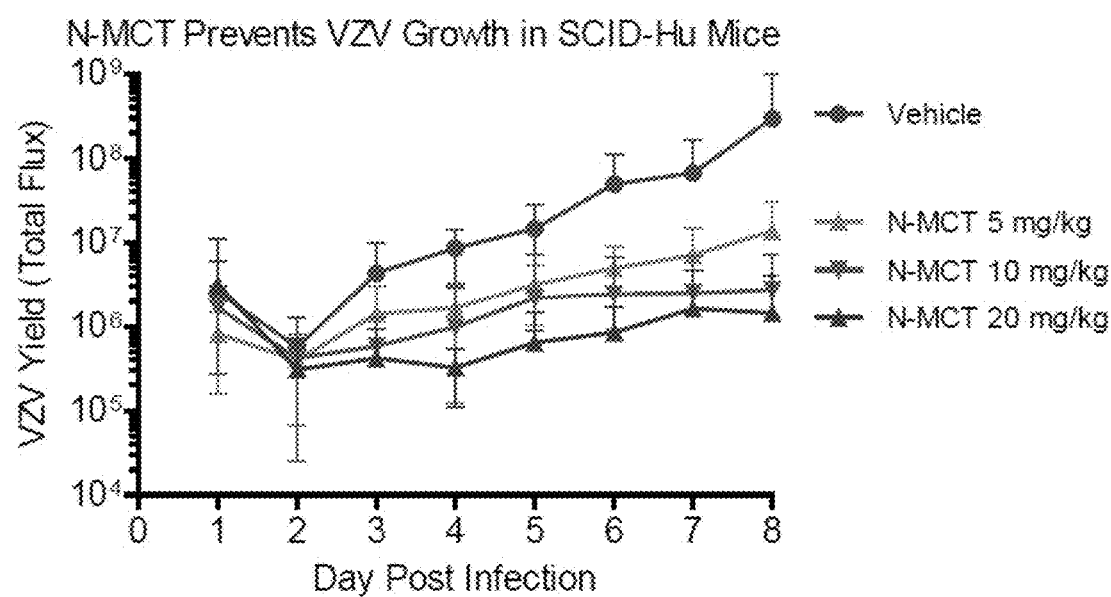

For oral administration, the deoxynucleoside analogs may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Tablets may contain the active compound in admixture with non-toxic pharmaceutically acceptable excipients including inert diluents such as calcium carbonate, sodium carbonate, lactose, calcium phosphate or sodium phosphate; granulating and disintegrating agents, such as corn starch; binding agents such as starch, gelatin or acacia; and lubricating agents such as magnesium stearate, stearic acid or talc. Tablets may be uncoated or coated by known methods to delay disintegration and absorption in the gastrointestinal tract and thereby provide a sustained action over a longer period of time. For example, a time delay material such as glyceryl monostearate may be used.

Preferably, the formulations for oral use may be presented as hard gelatin capsules wherein the active ingredient is mixed with an inert solid diluent, such as calcium carbonate, calcium phosphate or kaolin, or as soft gelatin capsules in which the active ingredient is mixed with water or an oil medium, such as peanut oil, liquid paraffin or olive oil.

Aqueous suspensions may contain the active ingredient in admixture with excipients suitable for the manufacture of aqueous suspensions. Such excipients include suspending agents, dispersing or wetting agents, preservatives, coloring agents and sweetening agents.

The N-MCT for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium.

The anti-VZV compositions of the invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, antipruritics, astringents, local anesthetics or anti-inflammatory agents), or may contain materials useful in physically formulating various dosage forms of the present invention, such as excipients, dyes, perfumes, thickening agents, stabilizers, skin penetration enhancers, preservatives or antioxidants. For assistance in formulating the compositions of the present invention, one may refer to Remington's Pharmaceutical Sciences, 15th ed., Mack Publishing Co., Easton, Pa. (1975) the entire contents of which are hereby incorporated by reference.

Therapy is initiated as early as possible following the onset of signs and symptoms. The administration route, amount administered and frequency of administration will vary depending on the age of the patient, condition to be treated, and severity of the condition. However, appreciating the effectiveness of N-MCT in the treatment of shingles, the disease may be rapidly cured with therapeutically effective doses for a duration of about one week.

Contemplated amounts, dosages and routes of administration for various herpesvirus infections by N-MCT will be quite different than established for the antiherpetic agent acyclovir, which is also a nucleoside analog. Detailed information relating to administration and dosages of acyclovir may be found in the Physician's Desk Reference, 47th edition, pp. 844-850, 1993 and in Hayden et al., "Antiviral Agents" in Basic Principles in the Diagnosis of Infectious Diseases, pp. 271-274), the entire contents of which are hereby incorporated by reference.

Briefly, contemplated amounts of N-MCT for oral administration to treat initial shingles range from about 600 to 2000 mg daily in a human. In case intensity of disease is severe, higher doses of N-MCT can be administered without any concern of toxicities along with topical application to enhance the response rate.

For topical treatment of shingles, a topical preparation containing about 50 mg N-MCT per gram of preparation is applied in an amount sufficient to adequately cover the affected area. The topical preparation is applied about every 6 hours daily for about 7 days or until the lesions have disappeared. The dose size per application will vary depending upon the total lesion area, but should approximate a one-half inch ribbon of preparation per four square inch surface area. Preferred concentration range may be from about 0.1 to about 5%, 0.1 to 4%, 0.1 to 3%, 0.1 to 2%, 0.1 to 1%, from about 0.2% to about 5%, 0.2 to 4%, 0.3 to 3%, 0.4 to 2%, 0.5 to 1%, from about 0.3 to about 5%, 0.3 to 4%, 0.3 to 3%, 0.3 to 2%, 0.3 to 1%, from about 0.4 to about 5%, 0.4 to 4%, 0.4 to 3%, 0.4 to 2%, 0.4 to 1%, from about 0.5 to about 5%, 0.5 to 4%, 0.5 to 3%, 0.5 to 2%, 0.5 to 1% and so forth. A variety of percentages of the compound within the topical formulation within this range may be used, even though the exact concentration may not be explicitly set forth herein, so long as the concentration falls within the range cited herein. The frequency of application to the affected site may be once per day or twice per day or three or four times per day depending on need.

For intravenous administration to treat VZV, about 10 mg/kg is infused at a constant rate over 1 hour, every 8 hours for about 7 days in adult patients (about 2,100 mg/day). For IV administration to treat VZV, about 1 mg/kg/8 h is administered for about 5 days initially and then can be increased to 5-10 mg/kg/8 hr (about 1,050-2,100 mg/day) to induce quick disease elimination.

The ranges of the administered amount of N-MCT to a human being may be calculated from doses expressed in terms of mg/kg from one species to an equivalent surface area dose expressed as mg/kg in the other species. This conversion formula is well-known in the art. This is seen in Reagan-Shaw et al., FASEB Journal, Vol 22, March 2007, pp. 659-661, which is incorporated by reference herein in its entirety and in particular as it relates to discussion of Km, as an example of the wide use of methods of correctly correlating the dosage from one animal species to other animal species.

The algorithm for dosage concentration for human beings can be extrapolated from another animal as follows. Km is a factor that converts mg/kg to mg/m².

Human applicable concentration (mg/kg)=(animal applicable concentration (mg/kg)×animal applicable Km index)/(human applicable Km index)

The USFDA provides the Km index of a human adult as 37, the Km index of a human child as 25, the Km index of mice as 3, and the Km index of a rat as 6. In the present application, the human applicable concentration of N-MCT may be calculated based on the Km values of the mice and the human adult.

The present invention also encompasses administering N-MCT using a variety of methods simultaneously, without limitation such as orally and topically and so forth.

The present invention is also directed to treating shingles, or reducing amount of varicella zoster virus (VZV) in a person identified as suffering from shingles, which steps include diagnosing a person for shingles onset, administering an effective concentration of N-MCT to the person diagnosed with shingles, preferably multiple times, and preferably multiple times per day, while optionally checking for progress of shingles treatment, and optionally stopping administering N-MCT when shingles has been treated. N-MCT may be administered in a variety of ways as discussed above, preferably simultaneously in at least two ways, such as orally and topically, but may be administered using one way.

The preferred compound in the present application is N-Methanocarbathymidine (N-MCT) as shown below.

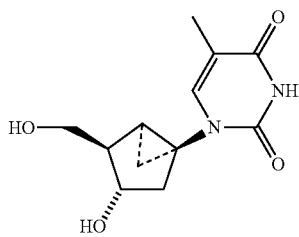

Effect of N-MCT on VZV Replication in Cultured Cells, Skin Organ Culture, and in a Mouse Model N-Methanocarbathymidine (N-MCT) is a thymidine analog that has antiviral activity in cultured cells against poxviruses, the gammaherpesvirus EBV, and the alphaherpesviruses HSV-1, HSV-2, and VZV (Prichard et al., 2006). We evaluated N-MCT against VZV in cultured cells, in skin organ culture (Taylor & Moffat, 2005), and in the SCID-Hu mouse model of VZV replication (Rowe et al., 2010). These assays were performed with the VZV-BAC-Luc strain, which expresses firefly luciferase. Virus spread in culture and in vivo was measured by bioluminescence imaging.

The present application discloses that N-MCT is highly potent in cultured cells with an $EC_{50}$ of 0.06 µM. N-MCT prevents VZV spread in human skin explants at concentrations>10 µg/mL. N-MCT prevents VZV spread in a mouse model of virus replication. Doses>10 mg/kg/day were more effective than control antiviral compounds (PAA, phosphonoacetic acid; PFA, phosphonoformic acid; and cidofovir). All doses were well tolerated by the mice and did not cause excessive weight loss.

Topical Administration and Delayed Treatment

Another objective of the invention was to evaluate N-MCT as a topical preparation. The skin organ culture system was developed here to test topical formulations of antiviral drugs (Rowe et al., 2010; Taylor and Moffat, 2005). Several ointments, ranging from hydrophobic to hydrophilic, were considered as vehicles for N-MCT. We found that N-MCT was effective at 0.5% in all ointments tested. N-MCT is effective as a topical treatment in human skin explants at concentrations as low as 0.05% in carbopol gel with 10% hydroxypropyl-β-cyclodextrin. N-MCT is highly effective as a topical treatment, even when VZV infection was established for 3-5 days. 10% hydroxypropyl-β-cyclodextrin has a moderate antiviral effect on VZV in skin organ culture. It is possible that the antiviral effect of N-MCT was potentiated by HPBCD.

Another objective was to determine whether delayed treatment was effective in vivo. It was important to know whether N-MCT is effective after VZV infection is established, which is usually when shingles is diagnosed. In this regard, in vivo study using SCID-Hu mouse model for N-MCT found that a relatively high dose, 50 mg/kg, was effective even when treatment began 7 days after virus inoculation. Moreover, N-MCT was well-tolerated in mice. Applicant has shown that even delayed treatment is effective to treat shingles.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—Preparation of VZV-BAC-Luc Inoculum

Human foreskin fibroblasts (HFFs) (CCD-1137Sk; American Type Culture Collection), used prior to passage 20 were grown in Eagle minimum essential medium with Earle's salts and L-glutamine (HyClone Laboratories), supplemented with 10% heat-inactivated fetal bovine serum (Benchmark FBS; Gemini Bio Products), penicillin-streptomycin (5000 IU/mL), amphotericin B (250 lg/mL), and nonessential amino acids (all Mediatech). VZV-BAC-Luc (Zhang et al., 2007), derived from the Parental Oka (POka, Accession number: AB097933) strain was propagated in HFFs. To prepare the virus for inoculation, VZV-infected HFFs were trypsinized, then washed and resuspended in TCM, and used immediately for direct injection. Each tissue was injected twice with 30 µL of the cell suspension using a 1 cc syringe fitted with a 27-gauge needle attached to a volumetric stepper (Tridak). The needle was lightly dragged across the tissue approximately 5 times to scarify the surface to increase infection. Tissues were incubated at 37° C. for 3 h to allow the virus to adhere, and then placed individually on NetWells that had contact with 1.0 mL of tissue culture medium. The cell-associated VZV inoculum was titered on MeWo cells (Taylor and Moffat, 2005) and was typically $1.5\times10^6$ pfu/mL, which is approximately $9\times10^4$ pfu/tissue.

Example 2—Evaluation of N-MCT in Cultured Cells

The first question we addressed was whether N-MCT was effective against VZV in cultured cells. A standard $EC_{50}$ evaluation was performed using the VZV-BAC-Luc strain and virus yield was measured by bioluminescence. HFFs were seeded in clear bottom, black-sided, 6-well plates (W1150, Genetix, Molecular Devices) 24 h prior to infection. Subconfluent HFFs were infected with cell-associated VZV-BAC-Luc showing more than 80% cytopathic effect (CPE) at 1:100 ratio of infected to uninfected cells and adsorbed for 2 h at 37° C. Excess virus was removed and the cells were washed once with PBS. Medium containing either DMSO diluent or serial 5-fold dilutions of N-MCT at concentrations between 0.000005 and 50.0 µg/mL were added; this point was deemed time zero. See Table 1.

TABLE 1

$EC_{50}$ Determination in HFFs

| N | Infected y or n | Compound | Concentration (µg/mL) | IVIS Scans |
|---|---|---|---|---|
| 5 | Y | Vehicle | 0 | 48 hpi |
| 5 |   | N-MCT | 0.000005 |   |
| 5 |   |   | 0.000026 |   |
| 5 |   |   | 0.000128 |   |
| 5 |   |   | 0.00064 |   |
| 5 |   |   | 0.0032 |   |
| 5 |   |   | 0.016 |   |
| 5 |   |   | 0.08 |   |
| 5 |   |   | 0.4 |   |
| 5 |   |   | 2.0 |   |
| 5 |   |   | 10 |   |
| 5 |   |   | 25 |   |
| 5 |   |   | 50 |   |

Cells were treated for 48 hpi (hour post infection) and the medium containing the drug was changed after 24 h. VZV spread was measured by bioluminescence imaging at 48 hpi and expressed as Total Flux (photons/sec/cm²/steradian). The 50% effective concentration ($EC_{50}$) values were calculated using two model systems, Yield-Density and Sigmoidal Models, by XLfit 5.3 software (ID Business Solution, idbs.com) and GraphPad Prism 5.02 for Windows (GraphPad Software, San Diego, Calif., graphpad.com). We confirmed that VZV is sensitive to N-MCT with an $EC_{50}$=0.06 µg/mL in human foreskin fibroblasts (Prichard et al., 2006). See FIG. 1.

Example 3—N-MCT Evaluation in Skin Organ Culture

Figure 2:
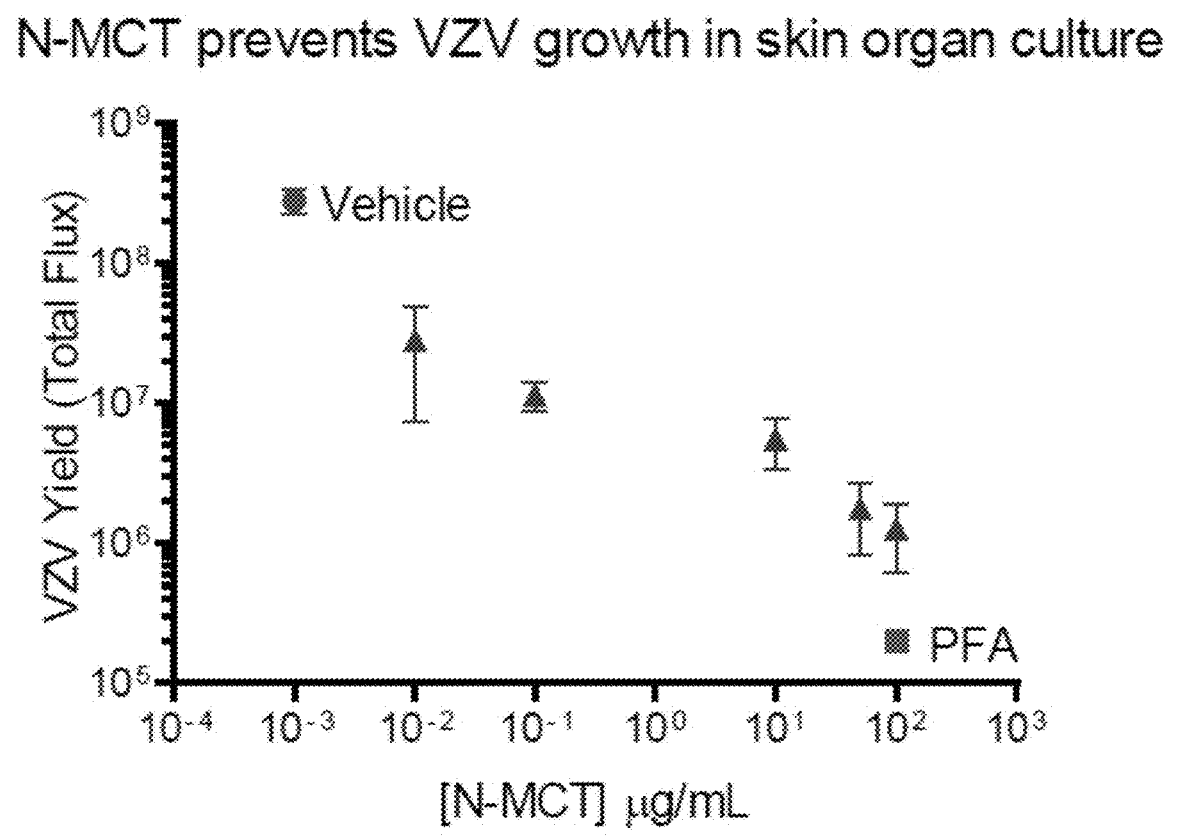

We also evaluated N-MCT in skin organ culture to determine whether it was equally potent in full-thickness skin. The antiviral effects of N-MCT were determined by assessing VZV yield on Day 5 or later compared to the inoculum on Day 1 for each individual piece of skin, and then these values were averaged and compared to the vehicle and positive control groups. In skin organ culture, higher concentrations of N-MCT were needed to reduce VZV spread; virus yield was reduced ~100-fold when [N-MCT] was greater than 10 µg/mL. See Table 2 and FIG. 2.

TABLE 2

Skin Organ Culture Assay

| N | Infected y or n | Compound | Dosage (µg/mL) | IVIS Scans |
|---|---|---|---|---|
| 6 | Y | Vehicle | 0 | Days 1 and 4 |
| 6 |   | PFA | 1 mM | Days 1 and 4 |
| 6 |   | N-MCT | 0.01 | (Refresh drug daily) |
| 6 |   |   | 0.1 |   |
| 6 |   |   | 1.0 |   |
| 6 |   |   | 10 |   |
| 6 |   |   | 25 |   |
| 6 |   |   | 50 |   |
| 6 |   |   | 100 |   |

Example 4—N-Methanocarbathymidine (N-MCT) is Effective In Vivo Against VZV in SCID-Hu Mice Example 4.1—SCID-Hu Mouse Model of VZV Replication CB.17 scid/beige male mice were implanted subcutaneously with human fetal skin (the same type of specimens used for the skin organ culture assay). After 3 weeks engraftment period, the skin implants were inoculated with VZV-BAC-Luc. The mice were divided into 5 groups of 12 mice: vehicle, positive control drug, N-MCT low dose, medium dose, and high dose (see FIGS. 3A, 3B, 4A and 4B). Treatment began approximately 2 hours after the inoculation surgery and was administered by oral gavage. Treatment continued twice daily (8:30 am and 8:30 pm) on Days 1-7. The mice were scanned in the IVIS-200 instrument daily from Day 1-8. The mice were weighed before the start of the study and daily during the treatment phase. See Table 3.

TABLE 3

SCID-Hu Mouse Assays

| N | Infected y or n | Compound | Dosage/day (mg/kg) | Tx Schedule |
|---|---|---|---|---|
| 12 | Y | Vehicle (water) | 0 | p.o. BID |
| 12 |   | PAA | 60 | i.p. BID |
| 12 |   | N-MCT | 5 | p.o. BID |
| 12 |   |   | 10 |   |
| 12 |   |   | 20 |   |
| 12 |   |   | 25 |   |
| 12 |   |   | 50 |   |
| 12 |   |   | 100 |   |

Example 4.2—Antiviral Effects of N-MCT

SCID-hu mice with human skin xenografts were infected intradermally with VZV and treated orally twice daily with vehicle, PFA (positive control), or N-MCT at 5, 10, 20, 25, 50, or 100 mg/kg/day. Virus spread was measured daily by in vivo bioluminescence imaging (IVIS). The antiviral effects of N-MCT were determined by assessing the VZV growth rate from Days 2-8 ($Log_{10}$ Total Flux/day) and by viral load on Day 8. The results were analyzed for statistical significance by ANOVA and Dunnett's post hoc test of multiple comparisons (GraphPad Prism). All doses of N-MCT and PFA significantly reduced VZV yield and growth rates ($p<0.0001$) compared to vehicle. N-MCT was evaluated in vivo using a range of doses from 5-100 mg/kg/day (p.o. BID), and all were effective. The optimal dose was approximately 20 mg/kg/day. See FIGS. 3A-3B and FIGS. 4A-4B.

These results were very encouraging for developing N-MCT as a therapeutic for VZV infections, particularly herpes zoster. Current therapy for zoster is oral acyclovir or brivudine (not in the U.S.), and foscarnet (i.v.) with very limited efficacy as a second line treatment (Whitley 1992). There are no topical antiviral agents currently approved for VZV infections. Zoster pain is often a long-lasting complication and is ameliorated by prompt antiviral therapy, thus there is a pressing need for antiviral drugs that are more effective than acyclovir and can be applied topically as well where virus replication is occurring.

Example 5—N-MCT as a Topical Antiviral Drug for VZV

The skin organ culture system is ideal for testing the effects of topical N-MCT on VZV replication. This study was important because N-MCT is likely to be a highly potent topical drug against VZV in skin. There is a large demand for new antiviral drugs that can limit the spread of VZV in skin, especially since the approved drugs do little to halt the replication of this virus. Moreover, treatment for shingles can combine the oral administration and topical administration, which could lessen PHN if virus spread was effectively stopped.

Example 5.1—Preparation of Carbopol Gel with N-MCT and Controls

Place 36 mL deionized sterile water into small beaker with stir bar. Slowly waft 900 mg of carbopol (980 NF, Lot # CCONLCC013, Lubrizol Corp) into water, avoiding clumps. Add equal volume N-MCT in 20% hydroxypropyl-β-cyclodextrin (Sigma) at 2× to reach the desired concentration. Add 2 drops NaOH (18% solution) to attain a pH near 5.0. Store at 4° C. The 0.5% cidofovir gel was made in a similar manner except that cidofovir was dissolved in water. The DMSO vehicle was prepared by adding a 2% DMSO solution in water to the carbopol suspension at a 1:1 ratio. Hydroxypropyl-β-cyclodextrin (HPBCD) was prepared by mixing 5.0 g with 20 mL sterile water. Stock solution of N-MCT was prepared by dissolving 90 mg N-MCT in 9 mL 20% HPBCD and sonicating for 1 min.

Example 5.2—Skin Organ Culture Topical Assay

Example 5.3—Assay #1—Dose Dependence

Topical N-Methanocarbathymidine (N-MCT) prevents VZV replication in skin. A skin organ culture model was used to evaluate N-MCT as a topical treatment for VZV. Human skin explants were inoculated with VZV by scarification and treated daily from 1-4 days post infection with N-MCT (0.05, 0.5, or 5%) or cidofovir (0.5%, positive control) in a carbopol gel. See Table 2 below.

Human fetal skin was purchased from ABR and delivered by overnight courier on wet ice. The tissue was cleaned, disinfected in betadine and 70% ethanol, then cut into pieces approximately 1-cm$^2$. Each piece was inoculated with VZV-BAC-Luc strain that expresses firefly luciferase. Approximately 3 hours after inoculation, the pieces of skin were placed in NetWells above tissue culture medium and incubated overnight. The next day (Day 1) each piece of skin was soaked in D-luciferin for 45 min, and then scanned in the IVIS-50 instrument to measure Total Flux, which is a correlate of VZV pfu. The drug treatment began on Day 1 or later by spreading an aqueous gel (carbopol) containing N-MCT at concentrations of 0.05, 0.5, or 5% (see Assay 1 in Table 4 below). One group of skin was treated with cidofovir (3% in carbopol gel) for a positive control. Each group contained 4-6 pieces of skin. The drug was applied daily until Day 5 (or other intervals), and then the skin pieces were scanned by IVIS to determine virus yield. The antiviral effects of N-MCT were determined by assessing VZV yield on Day 4 compared to the inoculum on Day 1 for each individual piece of skin, and then these values were averaged and compared to the vehicle and positive control groups. The results were analyzed for statistical significance by ANOVA and Dunnett's post hoc test of multiple comparisons (GraphPad Prism). All doses of N-MCT and cidofovir significantly reduced VZV yield (p<0.0004) compared to vehicle.

Figure 5A:
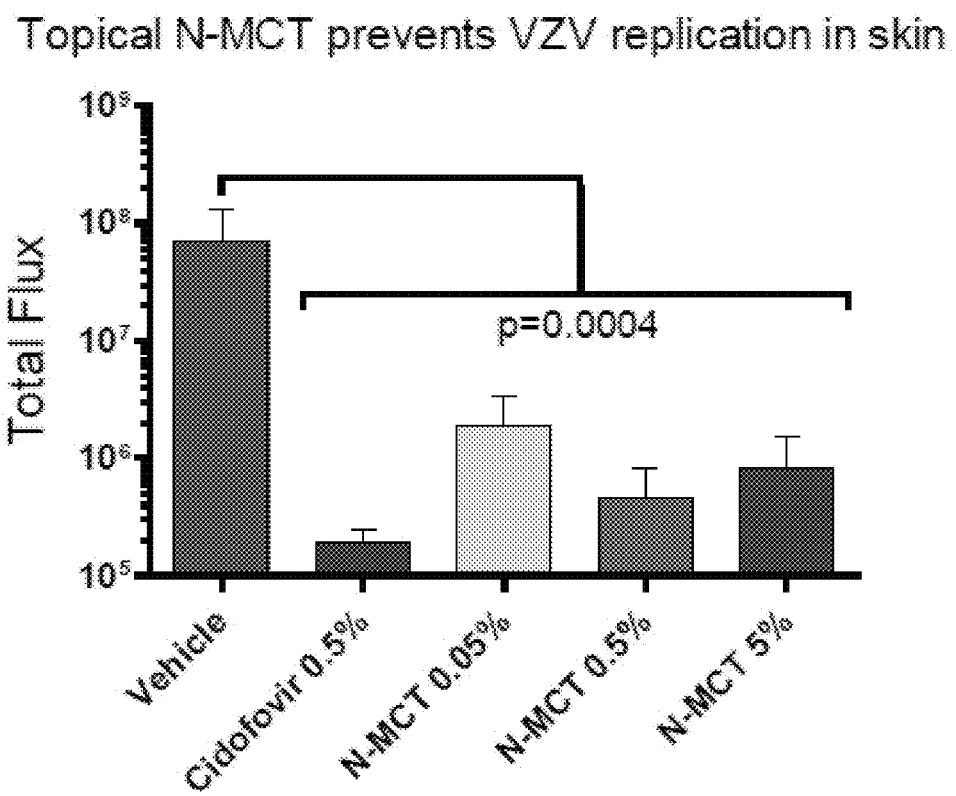
FIGS. 5A-5C show topical N-MCT prevents VZV replication in skin organ culture assay.

N-MCT prevented VZV replication when applied as a topical gel. All concentrations of N-MCT and the cidofovir control prevented VZV replication in skin explants. The treatments reduced virus yield by approximately 100-fold compared to the vehicle group. This reduction was significant (p=0.0004, One-way ANOVA, Dunnett's post hoc test). There was no difference between the treatments, although virus yield was highest in skin explants treated with the lowest concentration of N-MCT. See FIG. 5A.

TABLE 4

| N | Infected y or n | Compound | Topical Dosage (%) | IVIS Scans |
|---|---|---|---|---|
| Skin Organ Culture Assay 1: Dose dependence | | | | |
| 6 | Y | Vehicle | Carbopol only | Days 1 and 5 |
| 6 | | Cidofovir | 0.5% | (drug applied daily) |
| 6 | | N-MCT | 0.05% | |
| 6 | | | 0.5% | |
| 6 | | | 5.0% | |
| Skin Organ Culture Assay 2: Delayed treatment | | | | |
| 6 | Y | Vehicle | 10% HPBCD in Carbopol QD 1-4 dpi | Days 1, 5, 7, 9, 11 |
| 6 | | Cidofovir | 0.5% QD 1-4 dpi | |
| 6 | | N-MCT | 0.5% QD 1-4 dpi | |
| 6 | | | 0.5% QD 3-6 dpi | |
| 6 | | | 0.5% QD 5-8 dpi | |
| Skin Organ Culture Assay 3: Vehicle comparison | | | | |
| 4 | Y | Vehicle 1 | 10% HPBCD in Carbopol | Days 1 and 5 (drug applied daily) |
| 4 | | Vehicle 2 | 1% DMSO in Carbopol | |
| 4 | | N-MCT | 0.5% in Vehicle 1 | |
| 4 | | | 0.5% in Vehicle 2 | |

Example 5.4—Assay #2—Delayed Treatment

Figure 5B:
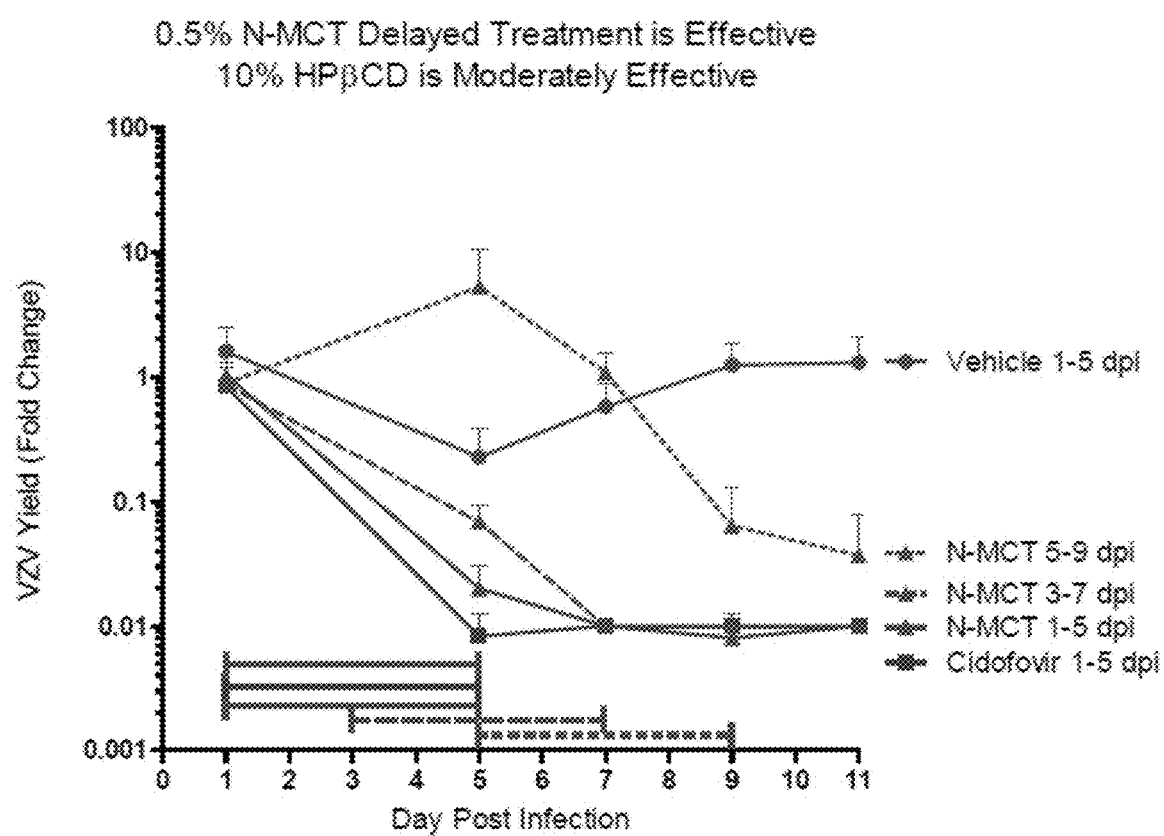

This assay differs from Assay 1 in that the Vehicle was prepared with 10% HPBCD, which is the solvent for the N-MCT. Refer to Assay #2 in Table 4 above. Three groups were treated on Days 1-4 and scanned on Day 5, which is the typical assay protocol. Two groups were treated after a delay of several days, which more closely reflects a clinical scenario of zoster. All treated groups received the same preparation of 0.5% N-MCT in carbopol with 10% HPBCD. VZV yield was reduced in the Vehicle group during the treatment phase, and then rebounded. This was likely due to the effects of HPBCD, which has known antiviral properties. The positive control group was treated with 0.5% cidofovir in carbopol (no HPBCD was added), and VZV yield was dramatically reduced during and after the treatment phase (cidofovir is no longer in clinical use in the U.S.). VZV yield was equally reduced in the group treated with N-MCT on Days 1-4 and no rebound was observed. Similarly, VZV yield was reduced to a similar low level by Day 7 in the group that was treated with N-MCT on Days 3-6. In contrast, VZV yield increased until Day 5 in the group that received no treatment until after this scan. The difference between this group and the Vehicle group was notable, since they were expected to be similar. As soon as N-MCT treatment began on Day 5, VZV yield decreased sharply. See FIG. 5B.

Example 5.5—Assay #3—Vehicle Comparison

Figure 5C:
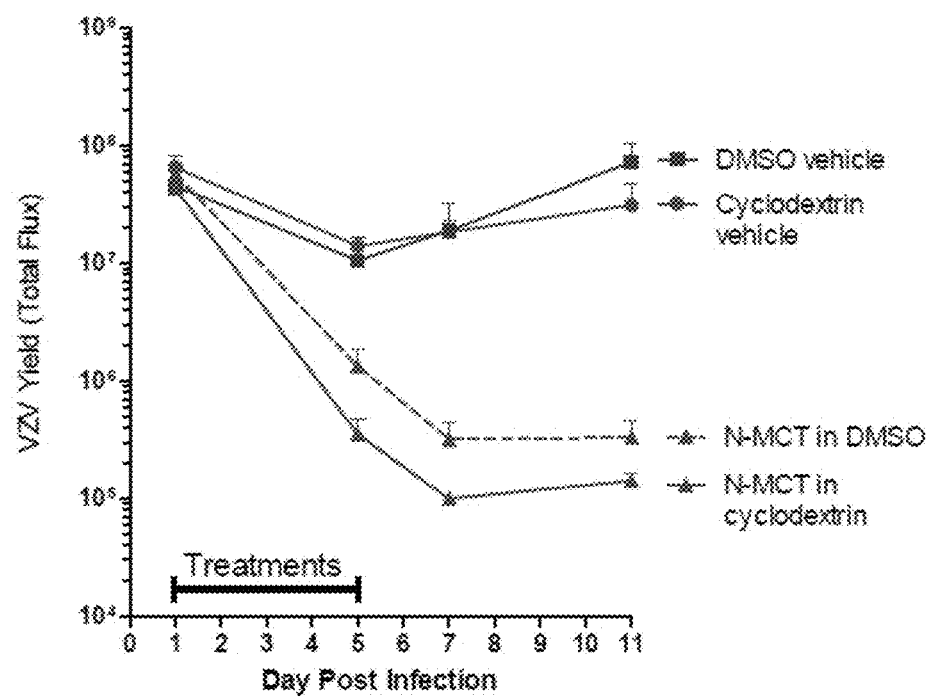

This assay compared two vehicles, 1% DMSO and 10% hydroxypropyl-β-cyclodextrin (HPBCD) in carbopol gel, and 0.5% N-MCT in either vehicle. Refer to Assay #3 in Table 4 above. Each group was treated on Days 1-4 and scanned on Day 5, which is the typical assay protocol. The skin specimens were then cultured without drug or vehicle for another 6 days (scans on Day 7 and Day 11) to observe virus rebound. VZV yield was reduced in both Vehicle groups during the treatment phase, and then rebounded. This was likely due to the effects of the slightly acidic carbopol gel. There was little difference between the two vehicles. Both groups treated with 0.5% N-MCT had a substantial decrease in VZV yield. The cyclodextrin preparation was slightly more effective than the DMSO prep. Importantly, there was no rebound in the groups treated with N-MCT. In fact, VZV yield continued to decrease after the treatment stopped. See FIG. 5C.

Example 6—Comparison of Topical Vehicles in Skin Organ Culture

Another objective of the invention was to test N-MCT at 0.5% in a variety of topical formulations in the SOC assay. The purpose was to determine the optimal topical formulation for N-MCT in full-thickness human skin. Human fetal skin was purchased from ABR and delivered by overnight courier on wet ice. The tissue was cleaned, disinfected in betadine and 70% ethanol, then cut into pieces approximately 1-cm². Each piece was inoculated with VZV-BAC-Luc strain that expresses firefly luciferase. Approximately 3 hours after inoculation, the pieces of skin were placed in NetWells above tissue culture medium and incubated overnight. The next day (Day 1) each piece of skin was soaked in D-luciferin for 45 min, and then scanned in the IVIS-50 instrument to measure Total Flux, which is a correlate of VZV pfu. The negative control group was not treated with drug or vehicle. The positive control drug treatment began on Day 1 by placing the skin, in NetWells, over medium containing 0.1 µg/mL N-MCT (see Table 5 below). The ointments were formulated with N-MCT by adding dry powder to the vehicle on a glass slab, then mixing thoroughly with a metal spatula. The ointments were warmed to 37° C. before spreading on the skin pieces with a Dacron swab. The test groups were treated topically with vehicles alone or ointments containing 0.5% N-MCT. Each group included 6 pieces of skin. The medium and drugs were refreshed daily. The final IVIS scan was on Day 5. The virus yield in each piece of skin was calculated by dividing the Total Flux measured on Day 5 by Day

TABLE 5

Skin Organ Culture Assays 4 and 5

| N | Infected y or n | Compound | Concentration | IVIS Scans |
|---|---|---|---|---|
| 6 | Y | Untreated | 0 | Days 1 and 5 |
| 6 | (1 skin | N-MCT | 0.1 µg/mL in medium | |
| 6 | specimen) | Aquaphor | 0 | |
| 6 | | N-MCT in Aquaphor | 0.5% Top | |
| 6 | | Eucerin | 0 | |
| 6 | | N-MCT in Eucerin | 0.5% Top | |
| 6 | Y | Untreated | 0 | Days 1 and 5 |
| 6 | (1 skin | N-MCT | 0.1 µg/mL in medium | |
| 6 | specimen) | Dermabase | 0 | |
| 6 | | N-MCT in Dermabase | 0.5% Top | |
| 6 | | Polybase | 0 | |
| 6 | | N-MCT in Polybase | 0.5% Top | |

Example 6.1—Assays #4 and #5

Assays 4 and 5 were repeated to improve the technique for applying the ointments to the skin pieces. We found that heating the ointment to 37° C. before applying caused less abrasion to the skin. The abrasion was likely the cause for the low yield of virus in the vehicle groups compared to the Untreated group. See FIGS. 6A, 6B, 7A and 7B. N-MCT (0.5%) was highly effective as a topical formulation in the SOC model. The ointments alone reduced VZV yield in these assays. There was no statistical difference between the ointments alone, and the effectiveness of N-MCT was equally potent in all formulations. After the IVIS scan on Day 5, no further treatments were applied.

Example 6.2—VZV Rebound after Topical N-MCT Treatment

To determine whether VZV rebounded after treatment stopped, the skin explants were scanned on Day 10. Virus yield increased in all samples, although the yield was 100-fold less in the groups treated with N-MCT. See FIG. 7C.

Example 7—Delayed N-MCT Treatment in SCID-Hu Mice

CB.17 scid/beige male mice were implanted subcutaneously with human fetal skin (the same type of specimens used for the skin organ culture assay). After 3 weeks engraftment period, the skin implants were inoculated with VZV-BAC-Luc ($5 \times 10^3$ pfu/implant). The mice were divided into 5 groups of 12 mice: vehicle, positive control drug cidofovir delayed to Days 4-11, N-MCT 50 mg/kg Days 0-7, Days 4-11, or Days 7-13 (see Table 6 below). Treatment began approximately 2 hours after the inoculation surgery and was administered by oral gavage. Treatment continued twice daily (8:30 am and 8:30 pm) on schedule. The previous studies in mice showed that N-MCT is most effective when given twice daily by mouth. The mice were scanned in the IVIS-200 instrument daily from Day 1-14. The mice were weighed before the start of the study and daily during the treatment phase. The antiviral effects of N-MCT were determined by assessing the VZV growth kinetics and rates ($Log_{10}$ Total Flux/day).

TABLE 6

SCID-Hu Mouse Assay

| N | Infected y or n | Compound | Dosage/day | Tx Schedule |
|---|---|---|---|---|
| 12 | Y | Vehicle | Water | p.o. BID 0-7 dpi |
| 12 | | Cidofovir | 10 mg/kg | i.p. QD 4-11 dpi |
| 12 | | N-MCT | 50 mg/kg | p.o. BID 0-7 dpi |
| 12 | | | 50 mg/kg | p.o. BID 4-11 dpi |
| 12 | | | 50 mg/kg | p.o. BID 7-13 dpi |

Statistical analysis: Data were analyzed using Student's t test or one-way ANOVA and Dunnett's Multiple Comparison post hoc tests. Calculations were made using GraphPad Prism 5.02 for Windows (GraphPad Software, San Diego, Calif., www.graphpad.com). A p<0.05 was considered statistically significant.

Example 8.1—Results and Discussion

Example 8.1.1—Mouse Weights and Mortality

The animals used in this experiment were SCID-beige mice purchased from Taconic (age 6-7 weeks). All the mice tolerated the oral gavage treatments. N-MCT was well tolerated and caused minimal weight loss. Some mice in each group appeared ill by the end of the study, which increased the variability in the weight data. This is typical in SCID mice. Data not shown.

Example 8.1.2—Effects of N-MCT on VZV Replication In Vivo

Figure 8A:
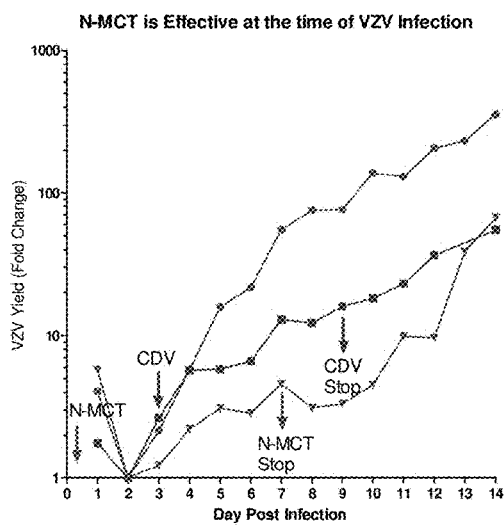
Figure 8B:
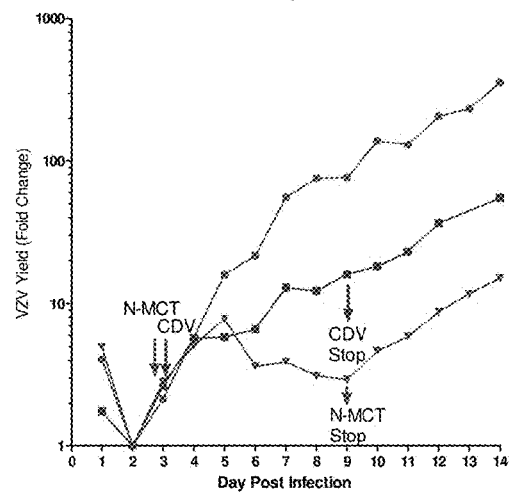
Figure 8C:
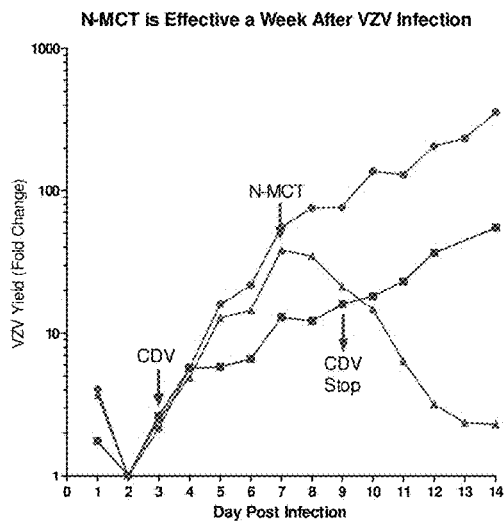

N-MCT is effective when treatment is delayed even 3 or 7 days after VZV infection. See FIGS. 8A-8C. 10% hydroxypropyl-β-cyclodextrin is known in the art to have a moderate antiviral effect on VZV in skin organ culture.

Based on all of the above results, Applicant makes the following conclusions. N-MCT is highly effective as a topical treatment, even when VZV infection has been established for 3-5 days. It is possible that the antiviral effect was potentiated by hydroxypropyl-β-cyclodextrin.

It is likely that the repeated swabbing of the skin surface removed infected cells, which lowered VZV yield in the treatment and vehicle groups. To increase penetration of D-luciferin on Day 5, the explants were washed briefly in PBS and then submerged in D-luciferin for 1 hour. All formulations were effective topical treatments for VZV. The most hydrophobic (Aquaphor) and the most aqueous (Dermabase) were equally effective.

N-MCT is well tolerated in vivo and treatment can be delayed up to one week after infection. The lowest effective dose has not yet been established.

All of the references cited herein are incorporated by reference in their entirety.

LITERATURE CITED

Andrei, G., Sienaert, R., McGuigan, C., De Clercq, E., Balzarini, J., Snoeck, R., 2005. Susceptibilities of several clinical varicella-zoster virus (VZV) isolates and drug-resistant VZV strains to bicyclic furano pyrimidine nucleosides. Antimicrobial agents and chemotherapy 49, 1081-1086.

Bernstein, D. I., Bravo, F. J., Clark, J. R., Earwood, J. D., Rahman, A., Glazer, R., Cardin, R. D., 2011. N-Methanocarbathymidine is more effective than acyclovir for treating neonatal herpes simplex virus infection in guinea pigs. Antiviral research 92, 386-388.

Hambleton, S., Steinberg, S. P., Gershon, M. D., Gershon, A. A., 2007. Cholesterol dependence of varicella-zoster virion entry into target cells. Journal of virology 81, 7548-7558.

Johnson, B. H., Palmer, L., Gatwood, J., Lenhart, G., Kawai, K., Acosta, C. J. 2015. Annual incidence rates of herpes zoster among an immunocompetent population in the United States. BMC Infect Dis 15: 502.

Kim, S. R., Khan, F., Tyring, S. K. 2014. Varicella zoster: an update on current treatment options and future perspectives, Expert Opin on Pharmacother, 15:1, 61-71.

Marquez, V. E., Hughes, S. H., Sei, S., Agbaria, R., 2006. The history of N-methanocarbathymidine: the investigation of a conformational concept leads to the discovery of a potent and selective nucleoside antiviral agent. Antiviral research 71, 268-275.

Prichard, M. N., K. A. Keith, D. C. Quenelle and E. R. Kern (2006). "Activity and mechanism of action of N-methanocarbathymidine against herpesvirus and orthopoxvirus infections." Antimicrob Agents Chemother 50(4): 1336-1341.

Quenelle, D. C., Collins, D. J., Rice, T. L., Rahman, A., Glazer, R., 2011. Efficacy of orally administered low dose N-methanocarbathymidine against lethal herpes simplex virus type-2 infections of mice. Antiviral chemistry & chemotherapy 22, 131-137.

Rowe, J., R. A. Arnold, C. White, J. Toli, C. K. Chu and J. Moffat (2010). "L-B-1-(5-Bromovinyl-2-hydroxymethyl-1,3-dioxolanyl) uracil (L-BHDU) prevents varicella-zoster virus replication in fibroblasts, skin organ culture, and SCID-Hu mice with human skin xenografts." Antiviral Res 86: A66.

Taylor, S. L. and J. F. Moffat (2005). "Replication of varicella-zoster virus in human skin organ culture." J Virol 79(17): 11501-11506.

Wang, W., S. L. Taylor, S. A. Leisenfelder, R. Morton, J. F. Moffat, S. Smirnov and H. Zhu (2005). "Human cytomegalovirus genes in the 15-kilobase region are required for viral replication in implanted human tissues in SCID mice." J Virol 79(4): 2115-2123.

Whitley, R. J. (1992). "Therapeutic approaches to varicella-zoster virus infections." J Infect Dis 166 Suppl 1: S51-57.

Zhang, Z., Rowe, J., Wang, W., Sommer, M., Arvin, A., Moffat, J., Zhu, H., 2007. Genetic analysis of varicella-zoster virus ORF0 to ORF4 by use of a novel luciferase bacterial artificial chromosome system. J. Virol. 81, 9024-9033.

Those skilled in the art will recognize, or be able to ascertain using no more than routine experimentation, many equivalents to the specific embodiments of the invention specifically described herein.

The invention claimed is:

1. A method of treating a Varicella-Zoster Virus (VZV) infection in an individual in need thereof, comprising the step of administering to said individual an effective Varicella-Zoster Virus antiviral amount of a compound called N-methanocarbathymidine (N-MCT), which has a northern configuration with the structure as follows

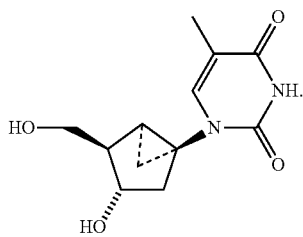

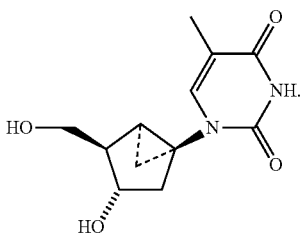

2. The method of claim 1, wherein said administering step is oral, intravenous, topical, intramuscular or subcutaneous.

3. The method of claim 2, wherein said administering is simultaneous.

4. The method of claim 2, wherein said administering step is oral.

5. The method of claim 1, wherein said oral amount for a human is between about 600 mg and about 2,000 mg per day.

6. The method of claim 2, wherein said oral amount for a human is between about 600 mg and about 1,500 mg per day.

7. The method of claim 2, wherein said administering step is intravenous.

8. The method of claim 2, wherein said administering step is topical.

9. The method of claim 8, comprising administering topical formulation after about 3 days after infection.

10. The method of claim 8, comprising administering topical formulation which comprises hydrophilic or hydrophobic ointment or cream.

11. A method of treating shingles in an individual in need thereof, comprising the step of administering to said individual an effective Varicella-Zoster Virus antiviral compound called N-methanocarbathymidine (N-MCT), which has a northern configuration with the structure as follows in a therapeutically effective dose.

12. A method of claim 11, wherein shingles is treated with optimal dose of N-MCT without postherpetic neuralgia (PHN) and debilitating pain.

13. The method of claim 11, wherein said administering step is oral, intravenous, topical, intramuscular or subcutaneous.

14. The method of claim 13, wherein said administering is simultaneous.

15. The method of claim 13, wherein said administering step is oral.

16. The method of claim 15, wherein said effective oral amount for a human suffering from symptoms of shingles is between about 600 mg and about 2,000 mg per day.

17. The method of claim 15, wherein said effective oral amount for a human suffering from symptoms of shingles is between about 600 mg and about 1,500 mg per day.

18. The method of claim 5, wherein said administering step is intravenous.

19. The method of claim 5, wherein said administering step is topical.

20. The method of claim 19, comprising administering topical formulation after about 3 days after infection.

21. The method of claim 19, comprising administering topical formulation which comprises hydrophilic or hydrophobic ointment or cream.

\* \* \* \* \*